United States Patent [19]

Park

[11] Patent Number: 5,010,207

[45] Date of Patent: Apr. 23, 1991

[54] PROCESS FOR THE PRODUCTION OF TRIMELLITIC ANHYDRIDE WITH SUPERIOR COLOR PROPERTIES

[75] Inventor: Chang M. Park, Naperville, Ill.

[73] Assignee: Amoco Corporation, Chicago, Ill.

[21] Appl. No.: 463,253

[22] Filed: Jan. 10, 1990

[51] Int. Cl.$^5$ .............................................. C07D 307/89
[52] U.S. Cl. .................................................... 549/245
[58] Field of Search ........................................ 549/245

[56] References Cited

U.S. PATENT DOCUMENTS

| | | | |
|---|---|---|---|
| 3,829,451 | 8/1974 | Decines et al. | 549/245 |
| 3,948,956 | 4/1976 | Handrick | 549/245 |
| 4,220,746 | 9/1980 | Puskas et al. | 549/245 |
| 4,587,350 | 5/1986 | Kilner et al. | 549/245 |
| 4,788,296 | 11/1988 | Robbins et al. | 549/245 |
| 4,797,497 | 1/1989 | Schammel | 549/245 |

FOREIGN PATENT DOCUMENTS 1948374 4/1970 Fed. Rep. of Germany .

OTHER PUBLICATIONS

Hayakawa et al., Chem. Abst. 72-132321b, (1970).

*Primary Examiner*—Cecilia Shen
*Attorney, Agent, or Firm*—Gunar J. Blumberg; William H. Magidson; Ralph C. Medhurst

[57] ABSTRACT

A process for the production of trimellitic anhydride with improved color properties disclosed. This process comprises treating trimellitic anhydride with an activated silicon compound followed by fractionation and at temperatures of about 200° to about 300° C. and a decreasing pressure of about 1 to about 25 mm Hg. Trimellitic anhydride is used in the manufacture of polyesters and polyamides-imides.

16 Claims, No Drawings

PROCESS FOR THE PRODUCTION OF TRIMELLITIC ANHYDRIDE WITH SUPERIOR COLOR PROPERTIES

BACKGROUND OF THE INVENTION

1. Field of the Invention

This invention relates to trimellitic acid anhydride (TMA) and more particularly is concerned with an improved process for the preparation of high purity trimellitic anhydride from trimellitic acid (TMLA). The invention has particular applicability when the trimellitic acid has been produced by the oxidation of a 1,2,4-aliphatic-substituted benzene with molecular oxygen in the liquid phase and in the presence of a heavy metal catalyst.

2. Background

Trimellitic acid, the 1,2,4 benzene tricarboxylic acid, is useful as an intermediate in the production of quality plasticizers and polyester resins. For these applications, in which trimellitic acid is esterified with a monohydric or a polyhydric alcohol, the evolution of water as an esterification byproduct together with the attendant difficulty of eliminating water from esterification reaction mixtures favors the desirability of employing trimellitic acid as the anhydride rather than as the acid. Resins and plasticizers may further require a trimellitic anhydride which is relatively free from color bodies and also free from the heavy metals employed as catalysts for the air oxidation of aliphatic-substituted benzenes to produce trimellitic acid. A Delta E color of below 1 is often specified for trimellitic anhydride used in white or transparent resins, and a metal content of less than about 50 p.p.m. (parts per million) is desirable to achieve good color and oxidation stability. While the more commonly employed maleic and phthalic acid anhydrides are readily prepared by thermal dehydration of the corresponding acids, and the anhydrides are easily purified by atmospheric pressure sublimation, trimellitic anhydride cannot be processed in this manner. Firstly, the acid requires temperatures in excess of 200° C. for thermal dehydration to take place, and even at these temperatures dehydration is not complete. Secondly, trimellitic anhydride is essentially nonvolatile and must be distilled at temperatures above 250° C. under vacuums on the order of 10-60 mm mercury absolute to prevent color degradation. Also, to increase the ordinarily-slow rate of dehydration, it has previously been proposed to employ chemical dehydrating agents such as acetic anhydride, sulfuric acid, phosphorus pentoxide, or the like to dehydrate the last traces of trimellitic acid before distilling the anhydride. These chemical dehydrating agents are costly to recover and regenerate and consequently impose an expensive operating burden on existing processes for the purification of trimellitic anhydride. Furthermore, their use in some cases results in the substitution of one impurity for another.

Accordingly, an object of the present invention is to provide an improved process for preparing high purity trimellitic anhydride from trimellitic acid having a Delta E color below 1.0 and a metal content below 50 p.p.m. Other and more particular objects will become apparent as the description of this invention is set forth in detail hereinafter.

Suitable silicon compounds include silica compounds activated in the purification process of trimellitic anhydride. Representative silicon compounds of this type include colloidal silica such as ammonia stabilized silicon sol in water and stabilized silica sol in hydrocarbon solvent. Silicon compounds which are not activated per se in the purification of trimellitic anhydride are suitably activated and are advantageously utilized in my novel process. Silicic acid is representative silicon compound which has to be activated. Silicon compounds of this type are activated by organic acids and anhydrides. Suitable organic acids and anhydrides are derived from aliphatic hydrocarbons. Preferred anhydrides have about 2 to 8 carbons atoms while preferred acids have 1 to 8 carbon atoms. Suitable acids and anhydrides include acetic acid, propionic acid, propionic anhydride, formic acid, maleic anhydride and 2-ethyl hexanoic acid. Acetic acid anhydride is the preferred activation agent for silicon compounds.

PRIOR ART

In the prior art German Patent Publication 19 48 374, trimellitic acid is treated with boric acid. In our improved process, trimellitic anhydride is treated in the presence of activated silicon compounds with a decreased pressure and distilled under further decreased pressure at a temperature of about 200° to about 275° C.

DETAILED DESCRIPTION OF THE INVENTION

In a preferred embodiment, about 0.1 to about 1.0 weight percent of an activated silicon compound is added and heated to a temperature of about 200° to about 300° C. for a period of about 30 to about 480 minutes, preferably about 60 to about 240 minutes in an inert gas atmosphere. After the addition of the silicon compound, the trimellitic anhydride is fractionated under a decreased pressure of about 1 to about 25 mm Hg, preferably about 5 to about 15 mm Hg. The silicon compound is activated by the addition of $C_2$–$C_8$ aliphatic anhydrides. The preferred anhydride being acetic anhydride and the preferred silicon compound being silicic acid.

Crude trimellitic acid may be prepared by the oxidation of various 1,2,4-aliphatic-substituted benzenes by way of several known routes. Chemical oxidizing agents such as nitric acid, chromic acid, potassium permanganate and the like can oxidize a tri-alkylbenzene such as pseudocumene directly to trimellitic acid. Rather than use chemical oxidizing agents, molecular or gaseous oxygen may be employed to effect a liquid phase oxidation of an aliphatic-substituted benzene in the presence of a heavy metal oxidation catalyst such as cobalt or manganese. In this manner, 1,2,4-trimethyl benzene is oxidized to trimellitic acid. Another process involving molecular-oxygen oxidation is the heavy-metal-catalyzed liquid phase oxidation of pseudocumene by repeatedly oxidizing one methyl radical to a carboxyl group, esterifying that carboxyl group with a lower alkanol, and oxidizing another methyl radical on the intermediated to another carboxyl group, followed by hydrolysis of the dialkanol ester of trimellitic acid to trimellitic acid. A more direct preparation is the one step oxidation of a trialkylbenzene such as pseudocumene with molecular oxygen in an inert liquid medium at about 150°-250° C. employing a catalyst comprising, in conjoint presence, a heavy metal oxidation catalyst and bromine. Suitable metal catalysts are selected from metals having atomic numbers of 13, 21-32, 39-51, 57-84 all inclusive, and the actinide earths, and may be added either in elemental form or as a soluble compound such as cobalt chloride, iron acetate, ammonium chromate, manganese acetyl acetonate, or the like. Likewise, bromine may be added as elemental bromine, HBr, sodium bromide, nickel bromide, benzyl bromide, etc. Trimellitic acid yields from the air oxidation of pseudocumene in the presence of a heavy metal oxidation catalyst and bromine are in excess of 160 weight percent.

To further illustrate various embodiments of the present invention several examples are provided hereinafter, it being understood that they are illustrative only.

EXAMPLE 1

Charged 250 grams of crude TMA to a 500 ml feed pot. Batch fractionation was started right away. The batch fractionation unit consisted of a 500 ml single-neck flask for the batch feed pot, one (1) inch ID glass column packed with $\frac{1}{4}$ inch ceramic saddles with a packing height of 11 inches, over-head vapor line connecting to the product receiver, and a 500 ml three-neck flask for the product receiver. The feed pot was equipped with a magnetic stirring bar for good agitation, a heating mantle for heating, and a thermometer. The packed column, over-head vapor line, and the product receiver were all electrically traced and insulated. Vacuum was pulled from the product receiver through a two-stage dry ice/acetone cold trap.

The fractionator heater was turned on to stabilize the temperature to the desired level. The vacuum pump was then turned on and maintained at around 5 mm Hg. The feed pot temperature was then further raised to an appropriate fractionation temperature. The product TMA was collected as an overhead condensate. The $\Delta E$ color of the TMA product was 2.69 compared to a typical commercial TMA color of 2.5 to 3.0.

EXAMPLE 2

Charged 250 grams of crude TMA to a feed pot along with 1.25 of silicic acid mixed with 5 ml of acetic anhydride. Without any delay, the material was batch fractionated following the similar procedure as described in Example 1. The $\Delta E$ color of the TMA product was 2.84. This shows that the addition of silicic acid to crude TMA is not effective in improving TMA color.

EXAMPLE 3

Into a watch glass of suitable size, charged 5 ml of acetic anhydride. Then, added 1.25 grams of silicic acid. The mixture was heated to boil off acetic anhydride. The dried powder thus obtained was charged to a 500 ml feed pot along with 250 grams of crude TMA. Batch fractionation started immediately following the similar procedure as described in Example 1.

The $\Delta E$ of the product TMA was 0.66, showing that an excellent product color can be obtained without heat soak when silicic acid is properly activated prior to the treatment.

EXAMPLE 4

Charged 250 grams of crude TMA to a feed pot. The material was heated to 180° C. With a gentle nitrogen gas sweep, 8 mls of LUDOX HS-40 was added dropwise to the feed pot. LUDOX HS-40 is an ammonia stabilized silica sol in water from DuPont. Then, batch fractionation started immediately following the similar procedure as described in Example. The resulting product had a $\Delta E$ color of 0.75.

EXAMPLE 5

Charges 250 grams of crude TMA to a feed pot. The material was heated to 180° C. With a gentle nitrogen gas sweep, 8 mls of NALCO CD-163, a hydrophobic colloidal silica in hexane, was added dropwise to the feed pot. The hexane solvent was immediately flashed off the feed pot. Batch fractionation then started following the similar procedure as described in Example 1. The resulting main product had a $\Delta E$ color of 0.91. Considering the amount of active silica gel in CD-163, CD-163 was very effective in reducing TMA color.

TMA DELTA E Procedure on the Milton Roy Color Scan II

The equipment setup in current use for the DELTA E procedure consists of a Milton Roy Color Scan II colorimeter, an Adds 1010 video monitor, and an IBM Proprinter. The printer is connected in a fashion to simply print out whatever appears on the Adds 1010 video monitor screen.

1. Start-Up Procedure
A. Initialization

During normal operation the instrument is turned on at all times (e.g., both when in use and when not in use). In this state only the LED indicator for the "INITIALIZE" button will be on. The lamp should be turned off when the unit is not being used in order to prolong lamp life. In the event of a power outgage/surge the Color Scan needs to be reinitialized. This is accomplished by simply pressing the "INITIALIZE" button (BLUE) on the instrument control panel. This procedure will clear all hardware and software flags and will set the microprocessor in default status. This key can be pressed whenever the operator wishes to abort all action and restart. The factory default settings are listed below along with the values used in the TMA DELTA E measurement.

| Default | TMA Setting |
|---|---|
| DF = 1 | DF = 2 |
| IL = 7 | IL = 1 |
| OB = 0 | OB = 0 |
| PR = 1 | PR = 0 |
| PT = 1 | PT = 3 |
| AV = 1 | AV = 1 |
| CR = 1 | CR = 1 |
| SC = 1 | SC = 1 |
| PF = 0 | PF = 1 |
| RF = 0 | RF = 0 |
| WS = 380 | WS = 380 |
| WE = 700 | WE = 700 |
| WI = 10 | WI = 10 |
| CLOW = 70 | CLOW = 40 |
| CHIGH = 130 | CHIGH = 150 |

To determine whether the variables are set to their proper values enter the command "CF" from the Adds Video Monitor. The variables will then be displayed on the screen and will be printed on the printer. To change a value simply type in the variable and the new value (e.g. type in DF=2 and press the return key).

B. Lamp

The lamp should be turned on for at least thirty minutes prior to calibration or performing measurements. To turn on the lamp, either press the "LAMP" (Green) button on the instrument control panel or enter the command "LAMPON" from the Adds Video Monitor. At the end of either command the LED indicator for the lamp on the instrument control panel will be on, indicating the command was carried out. After completing the measurements, the lamp should be turned off by either pressing the "LAMP" (green) button on the instrument control panel or entering the command "LAMPOFF" from the Adds Video Monitor. The LED indicator for the lamp will be off.

C. Calibration

The calibration procedure should be performed every day after the lamp has warmed up. This assures that calculations will be made against absolute values for reflectance measurements and 100% beam balance for transmittance measurements. The reference tile marked "R" and the sample tile marked "S" should be placed in their respective ports. Make sure all parameters are correctly set as described in Section A above. Open the transmission compartement and make sure that both the SPIN/SPEX slide and the small Area View Lever are in the "up" position. To calibrate the instrument simply press either the "CALIBRATE" (Yellow) button on the instrument control panel or enter the command "CA" from the Adds Video Monitor. During the calibration process, the LED indicator for the "CALIBRATE" button will be on. Upon completion of the command an asterisk will appear on the Adds Video Monitor screen and the LED indicator for the "CALIBRATE" button will be off.

In general, the instrument must be recalibrated any time the beginning wavelength (WS), the ending wavelength (WE) or the wavelength increment (WI) is changed. If not, a scan format error will be issued. Additionally, the instrument should be recalibrated when the calibration type (SC), the SPIN/SPEX Slide, or the optics are changed.

I claim:

1. The process for the production of trimellitic anhydride with improved color, the process comprising a treatment of trimellitic anhydride in the presence of a silicon compound selected from the group consisting of colloidal silica and silicic acid activated with an aliphatic acid or anhydride of from 1 to eight carbon atoms, selected from the group consisting of formic acid, acetic acid, propionic acid, 2-ethylhexanoic acid, acetic anhydride, propionic anhydride and maleic anhydride, said treatment at a temperature of from about 200° C. to about C., followed by fractionation at a temperature of about 200° to about 275° C. and a pressure of about 1 to about 25 mm mercury.

2. The process of claim 1 wherein the silicon compound is colloidal silica followed by fractionation at a temperature of about 200° to about 275° C. and a pressure of about 1 to about 25 mm mercury.

3. The process of claim 1 wherein the silicon compound is ammonia stabilized silica sol in water followed by fractionation at a temperature of about 200° to about 275° C. and a pressure of about 1 to about 25 mm mercury.

4. A process for the production of trimellitic anhydride with improved color, the process comprising a treatment of trimellitic anhydride in the presence of an activated silicon compound wherein said silicon compound is activated by treating with a $C_1$-$C_8$ aliphatic acid or anhydride selected from the group consisting of formic acid, acetic acid, propionic acid, 2-ethylhexanoic acid, acetic anhydride, propionic anhydride and maleic anhydride, at a temperature of from about 200° C to about 300° C. followed by fractionation at a temperature of about 200° to about 275° C. and a pressure of about 1 to about 25 mm mercury.

5. The process of claim 4 wherein the silicon compound is activated with an aliphatic acid or anhydride of from 1 to eight carbon atoms.

6. The process of claim 4 wherein the silicon compound is activated with an aliphatic acid of 1 to eight carbon atoms or anhydride of 2 eight carbon atoms.

7. The process of claim 4 wherein the silicon compound is activated with a $C_1$-$C_8$ aliphatic acid selected from the group consisting of formic acid, acetic acid, propionic acid and 2-ethylhexanoic acid.

8. The process of claim 4 wherein the silicon compound is activated with a $C_2$-$C_8$ aliphatic anhydride selected from the group consisting of acetic anhydride, propionic anhydride and maleic anhydride.

9. The process of claim 4 wherein the silicon compound is activated with acetic anhydride.

10. A process for the production of trimellitic anhydride with improved color, the process comprising treating trimellitic anhydride in the presence of activated silicic acid, at a temperature of from about 200° C. to about 300° C. followed by fractionation at a temperature of about 200° to about 275° C. and a pressure of about 1 about 25 mm mercury.

11. The process of claim 10 wherein silicic acid is activated with an aliphatic acid or anhydride selected from the group consisting of formic acid, acetic acid, propionic acid, 2-ethylhexanoic acid, acetic anhydride, propionic anhydride and maleic anhydride.

12. The process of claim 10 wherein the silicic acid is activated with an aliphatic acid of 1 to eight carbon atoms or anhydride of 2 to eight carbon atoms.

13. The process of claim 10 wherein the silicic acid is activated by treating it with $C_1$-$C_8$ aliphatic acids selected from the group consisting of formic acid, acetic acid, propionic acid, and 2-ethylhexanoic acid.

14. The process of claim 10 wherein the silicic acid is activated with $C_2$-$C_8$ aliphatic anhydrides selected from the group consisting of acetic anhydride, propionic anhydride and maleic anhydride.

15. The process of claim 10 wherein the silicic acid is treated with acetic anhydride.

16. A process for the production of trimellitic anhydride with improved color, the process comprising treating trimellitic anhydride in the presence of stabilized silica sol in a hydrocarbon solvent at a temperature of from about 200° C. to about 300° C., followed by fractionation at a temperature of about 200° to about 275° C. and a pressure of about 1 to about 25 mm mercury.

* * * * *

UNITED STATES PATENT OFFICE
CERTIFICATE OF CORRECTION

Patent No. 5,010,207              Dated April 23, 1991

Inventor(s) Chang Man Park

It is certified that error appears in the above-identified patent and that said Letters Patent is hereby corrected as shown below:

| Col. | Line | |
|------|------|---|
| 2 | 59 | "intermediated" should read --intermediate-- |
| 4 | 3 | "Charges" should read --Charged-- |
| 5 | 16 | "compartement" should read --compartment-- |
| 5 | 46 | "about C." should read --about 300°C-- |

Signed and Sealed this

Fifteenth Day of September, 1992

Attest:

DOUGLAS B. COMER

Attesting Officer

Acting Commissioner of Patents and Trademarks